United States Patent [19]

Meyer et al.

[11] Patent Number: 4,971,661
[45] Date of Patent: Nov. 20, 1990

[54] PURIFICATION OF PROPYLENE OXIDE USING AN AQUEOUS ACETONE EXTRACTIVE DISTILLATIN AGENT

[75] Inventors: Robert A. Meyer, Austin; Kenneth P. Keating, Georgetown; William A. Smith, Austin; Robert M. Steinberg, Houston, all of Tex.

[73] Assignee: Texaco Chemical Company, White Plains, N.Y.

[21] Appl. No.: 424,423

[22] Filed: Oct. 20, 1989

[51] Int. Cl.$^5$ .................. B01D 3/40; C07D 301/02
[52] U.S. Cl. .................................. 203/54; 203/62; 203/78; 203/79; 203/80; 203/84; 203/92; 549/541
[58] Field of Search ................. 203/54, 62, 96, 97, 203/92, 93, 78–80, 84, 85, 14; 549/541; 568/411

[56] References Cited

U.S. PATENT DOCUMENTS

| | | | |
|---|---|---|---|
| 2,622,060 | 12/1952 | Robeson et al. | 203/37 |
| 3,059,037 | 10/1962 | Cahn | 203/54 |
| 3,350,418 | 10/1967 | Bowe et al. | 549/541 |
| 3,632,482 | 1/1972 | Hoory et al. | 203/56 |
| 3,715,284 | 2/1973 | Burns et al. | 203/62 |
| 3,881,996 | 5/1975 | Schmidt | 549/541 |
| 4,140,588 | 2/1979 | Schmidt | 203/96 |
| 4,243,492 | 1/1981 | Yamamura et al. | 549/541 |
| 4,304,639 | 12/1981 | Hardy et al. | 549/541 |

FOREIGN PATENT DOCUMENTS 1210190 10/1970 United Kingdom ............... 549/541

Primary Examiner—Wilbur Bascomb
Attorney, Agent, or Firm—Jack H. Park; Kenneth R. Priem; Carl G. Ries

[57] ABSTRACT

An impure propylene oxide feedstock contaminated with from about 50 to about 1000 ppm of methanol and from about 0 to about 1 wt. % of acetone is charged to the lower half of an extractive distillation column containing at least about 25 theoretical plates and an extractive distillation agent consisting essentially of a blend of acetone and water (acetone/water blend) containing about 20 to about 30 wt. % of acetone and, correspondingly, about 80 to about 70 wt. % of water is charged to the tower at a point 4 to 7 theoretical stages above the impure propylene oxide feed point; the extractive distillation agent being introduced into the extractive distillation column in the ratio of said feedstock to said extractive distillation agent of from about 5:1 to about 20:1, whereby an overhead distillate fraction is obtained consisting essentially of propylene oxide contaminated with not more than about 60 ppm of methanol, not more than about 0.02 wt. % of acetone and not more than about 0.3 wt. % of water.

6 Claims, 1 Drawing Sheet

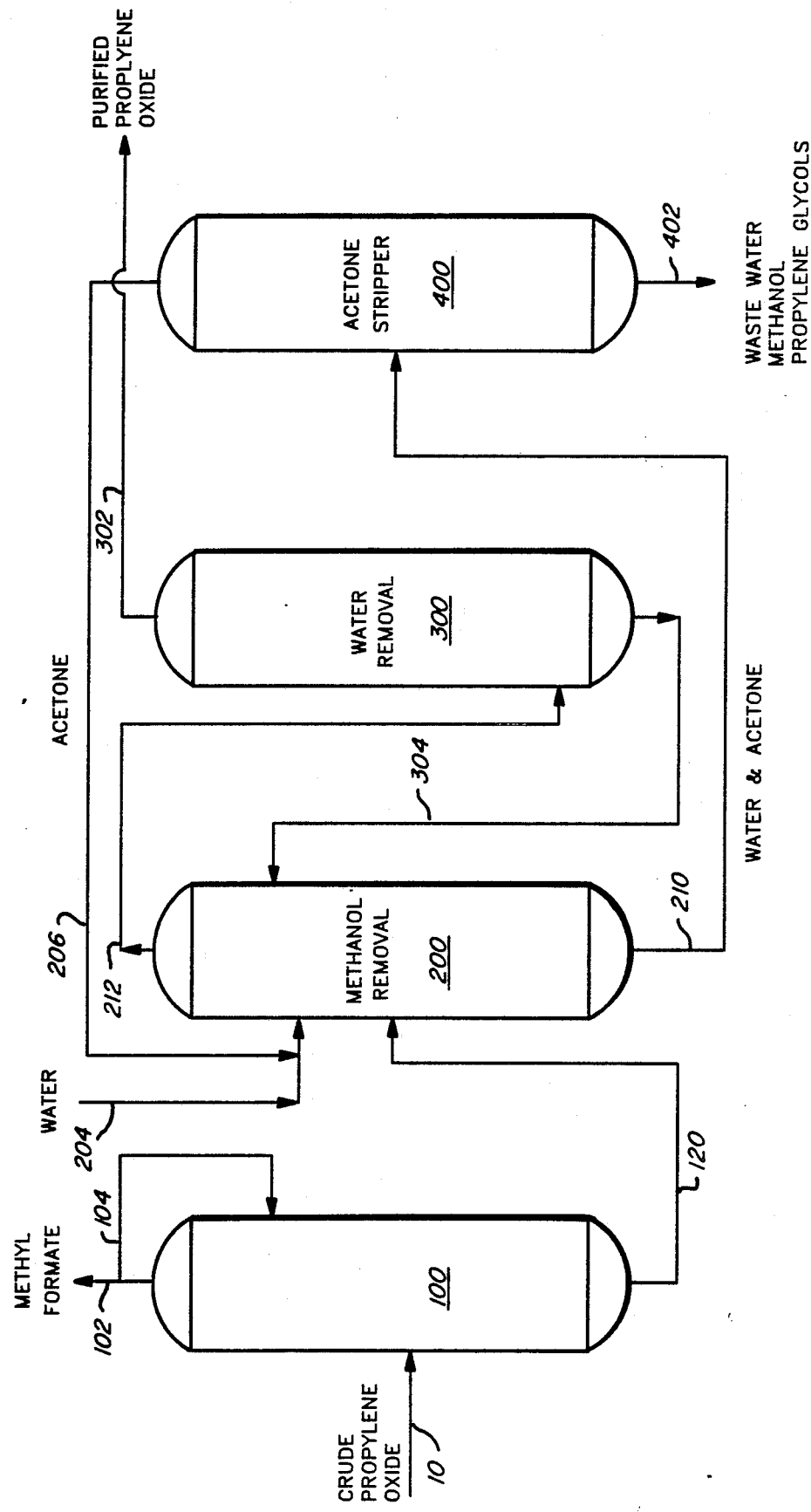

PURIFICATION OF PROPYLENE OXIDE USING AN AQUEOUS ACETONE EXTRACTIVE DISTILLATIN AGENT

BACKGROUND OF THE INVENTION

1. Field of the Invention

This invention relates to the purification of propylene oxide. More particularly, this invention relates to a distillation process for removing contaminating quantities of methanol and, if present, acetone, from an impure propylene oxide feedstock. Still more particularly, this invention relates to a method wherein an impure propylene oxide feedstock contaminated with from about 50 to about 1000 ppm of methanol and from about 0 to about 1 wt. % of acetone is purified in an extractive distillation column using an extractive distillation agent consisting of an acetone/water blend ranging from about 20 to 30 wt. % acetone and, correspondingly, 80 to 70 wt. % water.

2. Prior Art

It is known to react a hydroperoxide feedstock such as tertiary butyl hydroperoxide with propylene in the presence of an epoxidation catalyst in order to provide a reaction product comprising propylene oxide, an alcohol corresponding to the hydroperoxide feedstock, a solvent, and impurities (see, for example, Kollar U.S. Pat. No. 3,350,422, Kollar U.S. Pat. No. 3,351,635 and Sorgenti U.S. Pat. No. 3,666,777.

It is also known to separate the reaction product by distillation in order to obtain a plurality of fractions including, for example, a propylene recycle fraction, a propylene oxide product fraction, an alcohol fraction, etc.

It is also known that methanol is a common contaminant for propylene oxide which is removed only with difficulty.

For example, Mitchell et al. U.S. Pat. No. 2,550,847 is directed to a process for separating purified propylene oxide from a crude propylene oxide product contaminated with acetaldehyde, methyl formate, methanol, etc., by treating the crude mixture with an aqueous basic substance followed by recovery of the purified propylene oxide by any suitable means such as by decantation. Mitchell et al. reported a recovery of a product containing 78 to 82 wt. % of propylene oxide which, they stated, could be increased in purity to about 95 to 99% by fractional distillation.

Robeson et al. U.S. Pat. No. 2,622,060 discloses a process for the purification of propylene oxide contaminated with impurities, including methanol, by subjecting the impure propylene oxide to distillation in the presence of an extractive distillation agent comprising an aqueous solution of an alkali. The inventors report in Example 1 of their patent a method wherein 500 parts by weight of a crude propylene oxide fraction was extractively distilled in accordance with their invention to obtain 325 parts by weight of a product containing about 99.6 wt. % of propylene oxide. Thus, a significant loss of propylene oxide occurred during the process.

In a process unrelated to the purification of propylene oxide, Goddin et al. in U.S. Pat. No. 2,751,337 disclose a process for separating acetone from a mixture of acetone with methanol and methyl acetate utilizing water as an extractive distillation agent.

Hamlin et al. in U.S. Pat. No. 3,409,513 disclose the hydro-extractive distillation of mixtures comprising acetone, lower aliphatic alcohols and esters of lower aliphatic alcohols with carboxylic acids. It is pointed out by the patentees that acetone, methyl acetate and methanol form an azeotrope boiling at 55.5-56.5° C. Hamlin et al. propose to recover partially purified acetone from such a ternary azeotrope by liquid-liquid extraction with water followed by hydro-extractive distillation of the aqueous phase in order to obtain a partially purified acetone fraction.

Washall U.S. Pat. No. 3,578,568 discloses a process for removing oxygen-containing impurities such as acetone, acetaldehyde and methanol from impure propylene oxide using a glycol such as ethylene glycol or propylene glycol as an extractive distillation agent.

Hoory and Newman U.S. Pat. No. 3,632,482 is directed to a propylene oxide recovery process by extractive distillation using an alcohol-ketone-hydrocarbon solvent. The invention relates to a method for the purification of crude propylene oxide contained in a mixture produced by the epoxidation of propylene with an organic hydroperoxide and calls for extractive distillation of the crude propylene oxide in a plurality of successive extractive distillation zones with the aid of a solvent mixture consisting essentially of hydrocarbons, alcohols, and/or ketones corresponding to the organic hydroperoxide employed in producing the propylene oxide. In the preferred embodiment of their invention, the extractive distillation agent is a recycle fraction from a three column distillation sequence wherein the bottoms from the third distillation column are flashed to obtain an overhead composed of hydrocarbons, alcohols and/or ketones which is recycled as an extractive distillation agent to the three distillation columns involved in the propylene oxide purification sequence.

Burns et al. U.S. Pat. No. 3,715,284 discloses a process for the purification of impure propylene oxide using acetone or a mixture of acetone with methanol which is introduced into a distillation column either below or together with the impure propylene oxide.

Schmidt U.S. Pat. No. 3,881,996 is directed to a distillation sequence employing at least three and optionally four columns for the purification of crude propylene oxide, one of the columns optionally being an extractive distillation column wherein a hydrocarbon such as octane is used as the extractive distillation agent.

Schmidt U.S. Pat. No. 4,140,588 discloses a process for the purification of propylene oxide contaminated with methanol and acetone using water as an extractive distillation agent, the water being introduced into the distillation column above the point of introduction of the crude propylene oxide feed.

Schmidt states at column 2, lines 50-55 that: "Propylene oxide, however, has a substantial solubility in water and is readily hydrolyzed to propylene glycol (PG) in the presence of large amounts of water"—i.e., in the reboiler section of the tower.

The presence of additional acetone (added to feed or solvent) in accordance with the present invention serves as a buffer between the reboiler section and the balance of the tower. This is apparent if one looks at the normal boiling points (i.e., atmospheric pressure):

| Component | NBP (°C.) |
| --- | --- |
| Propylene Oxide (PO) | 34 |
| Acetone | 56 |
| Water | 100 |

The acetone serves as a buffer section in the tower between the PO and water (a high concentration of water is in the reboiler and a high concentration of PO is above the acetone buffer zone). The acetone buffer zone limits the contact of PO with a high concentration of water. It is apparent that the additional acetone makes its presence known in the reboiler as well as evidenced by lower reboiler temperatures. This also helps reduce PO to PG conversion as the reaction rate increases with increasing temperature. Any PO making its way to the reboiler will see a lower temperature, thus reducing its conversion to PG.

It is clear that the tower should be operated at as low a pressure as is practical to minimize PO loss.

Seifert et al. U.S. Pat. No. 4,369,096 is directed to a process for the purification of epoxides wherein the purification is effected by treatment with compounds containing at least one primary amine group.

SUMMARY OF THE INVENTION

In accordance with the present invention, an impure propylene oxide feedstock contaminated with from about 50 to about 1000 ppm of methanol and from about 0 to about 1 wt. % of acetone is charged to the lower half of an extractive distillation column containing at least about 25 theoretical plates and an extractive distillation agent consisting essentially of a blend of acetone and water (acetone/water blend) containing about 20 to about 30 wt. % of acetone and, correspondingly, about 80 to about 70 wt. % of water is charged to the tower at a point 4 to 7 theoretical stages above the impure propylene oxide feed point. The extractive distillation agent is introduced into the extractive distillation column in the ratio of said feedstock to said extractive distillation agent of from about 5:1 to about 20:1, whereby an overhead distillate fraction is obtained consisting essentially of propylene oxide contaminated with not more than about 60 ppm of methanol, not more than about 0.02 wt. % of acetone and not more than about 0.3 wt. % of water.

BACKGROUND OF THE PRESENT INVENTION

When propylene is reacted in liquid phase with an organic hydroperoxide such as tertiary butyl hydroperoxide in solution in a solvent such as tertiary butyl alcohol in the presence of a soluble epoxidation catalyst such as a molybdenum oxidation catalyst, a reaction mixture is formed comprising propylene oxide, an alcohol corresponding to the organic hydroperoxide feedstock and impurities including methyl formate, acetaldehyde, acetone and methanol. A minor amount of water will also frequently be present in the reaction mixture.

It is known to separate the epoxidation reaction product formed by the reaction of propylene with tertiary butyl hydroperoxide in solution with tertiary butyl alcohol in the presence of a soluble molybdenum catalyst to provide a recycle propylene fraction, an impure propylene oxide fraction and a heavier tertiary butyl alcohol fraction.

Although the impure propylene oxide obtained in this fashion will normally be composed of about 95 wt. % or more of proplene oxide, the oxygen-containing impurities such as those mentioned above, are removed from the propylene oxide only with difficulty.

Although it is known that methanol can be removed from propylene oxide by extractive distillation using water as an extractive distillation solvent as shown, for example, by Schmidt U.S. Pat. No. 4,140,588, a significant disadvantage of the Schmidt process is the noticeable loss of propylene oxide during the purification step, principally by hydration with water, this loss amounting to as much as about 5 to about 10 wt. % of the propylene oxide initially charged to the purification zone.

It has been discovered in accordance with the present invention, however, that when the impure propylene oxide feedstock fed to an extractive distillation zone contains a minor amount of methanol, the methanol can be removed therefrom by extractive distillation without significant loss of propylene oxide when the extractive distillation agent consists essentially of a mixture of an acetone/water blend consisting of 20–30 wt. % acetone.

BRIEF DESCRIPTION OF THE DRAWING

The drawing is a schematic flow sheet with conventional parts omitted showing the general recovery sequence that is used in accordance with the present invention in purifying propylene oxide.

In the drawing, for convenience, the present invention is illustrated in connection with a process wherein the propylene oxide is prepared by the epoxidation of propylene with tertiary butyl hydroperoxide to provide a reaction product comprising propylene oxide and additional tertiary butyl alcohol formed. It will be understood that, if desired, other hydroperoxides such as ethyl benzene hydroperoxide, tertiary amyl hydroperoxide, etc., may be used in the preparation of propylene oxide.

DESCRIPTION OF THE PREFERRED EMBODIMENT

Turning now to the drawing, there is shown a schematic flow sheet illustrating a preferred method of practicing the process of the present invention. In the drawing, conventional parts such as valves, pumps, temperature sensors, pressure sensors, heaters, coolers, flow control regulation apparatus, reboilers, reflux condensers, etc., have been omitted.

In accordance with a preferred embodiment of the present invention, propylene oxide is separated in a first distillation zone (not shown) from other components of an epoxidation reaction mixture in order to provide an impure propylene oxide fraction contaminated with oxygen-containing impurities such as acetaldehyde, methyl formate, propionaldehyde, acetone, methanol, isopropanol, tertiary butyl alcohol, etc.

The impure propylene oxide feedstock that is thus provided from the first distillation zone is then purified in a second distillation zone, which in accordance with the preferred embodiment of the present invention, comprises four distillation columns, each of which is equipped with an appropriate reflux condensing means and an appropriate reboiler heating means.

Thus, in accordance with the present invention, an impure propylene oxide fraction contaminated with impurities including methyl formate, acetaldehyde, acetone, methanol and water is charged by a charge line 10 to a first distillation column 100 which is operated so as to remove methyl formate as an overhead distillate fraction by way of a methyl formate discharge line 102, the methyl formate also containing substantially all of the acetaldehyde initially present in the fraction 10. In accordance with this embodiment, the first distillation column 100 is operated at a pressure of about 10 to about 70 psig. with a reboiler temperature of about 50 to about 90° C. and a top reflux temperature of about 40 to about 80° C., the distillation conditions being selected so as to obtain substantially complete removal of the acetaldehyde and methyl formate impurities overhead by way of a line 102. A portion of the fraction 102 is returned to the tower 100 as reflux by line 104.

The heavier distillation fraction 120 discharged from the column 100, comprises substantially all of the propylene oxide charged to the distillation column 100 by the charge line 10 and is contaminated with from about 50 to about 1000 ppm of methanol and from 0 to about 1 wt. % of acetone; the heavier fraction being discharged by way of a line 120 leading to a second distillation column 200 which, in accordance with the present invention, will preferably be a column containing at least about 25 theoretical plates and more preferably, from about 30 to about 50 theoretical plates. The column 200 is suitably operated under distillation conditions including a pressure of about 0 to 30 psig., a reflux ratio of from about 5:1 to about 10:1, a reboiler temperature within the range of about 60° to about 100° C. and a top temperature of about 35° to about 70° C.

The impure propylene oxide is preferably charged to the distillation column 200 in the lower half thereof. An extractive distillation agent composed of an acetone/water blend consisting of 20–30 wt. % acetone and 80–70 wt. % of water is charged to the upper half of the distillation column 200 by an extractive distillation charge line 202 to which water is charged by a line 204 and to which acetone is charged by a recycle line 206. Reflux is provided by a recycle fraction 304 obtained in a manner to be described.

Within the distillation column 200, substantially all of the methanol, water and acetone introduced into the column 200 by the line 120 and the extractive distillation agent charge line 202 are removed as a heavier distillation fraction 210 and a partially purified propylene oxide fraction is removed overhead by a line 212, the partially purified propylene oxide fraction containing not more than about 60 ppm of methanol, not more than about 0.02 wt. % of acetone and not more than about 0.3 wt. % of water.

The thus further purified propylene oxide in the line 212 is charged to a third distillation column 300 which is suitably operated under distillation conditions, at about atmospheric pressure including a reflux temperature of about 40 to about 45° C. and a reboiler temperature of about 45 to about 50° C. selected to provide a purified substantially anhydrous propylene oxide distillate fraction which is withdrawn by way of an overhead line 302 and a recycle fraction 304 comprising water and acetone and residual amounts of methanol, if any, which is recycled to the distillation column 200 as reflux as noted above.

The heavier distillation fraction 210 from the column 200 comprising water, methanol and acetone is charged to a fourth distillation column 400 wherein the acetone is separated overhead as a distillate fraction 206 for recycle to the extractive distillation column 200 by way of the extraction agent charge line 202.

A heavier distillation fraction 402 is discharged from the distillation column 400 comprising heavier impurities such as water, methanol, propylene glycols, etc.

The fourth distillation column 400 is operated under distillation conditions including a reflux temperature of about 60° to about 65° C., a reboiler temperature of about 115° to about 125° C. and at about atmospheric pressure.

EXAMPLES

The invention will be further illustrated by the following specific examples which are given by way of illustration and not as limitations on the scope of this invention. Where parts are mentioned, they are parts by weight.

Table I is a summary of distillation conditions. The percent methanol reduction with respect to the feed in the overhead product is given and the consequent loss of propylene oxide is also set forth. The percent propylene oxide lost is that which is converted to propylene glycol plus that leaving the bottom of the tower as propylene oxide.

Trial 6204-09-20 is a control experiment at 36 psia when water was used as the extractive solvent. In Trials 6204-25-14, 6204-25-24 and 6204-24-30, an acetone/water blend was used as the solvent. Up to a four-fold reduction in propylene oxide loss was achieved.

Trial 6204-08-05 is the control experiment at 18 psia when water was used as the extractive solvent. In Trial 6204-28-20 an acetone/water blend was used as the solvent. An eight-fold reduction in propylene oxide loss is apparent.

In Experiments 6204-18-28 and 6243-14-08, a mixture containing only methanol and propylene oxide was used as the feed. In trial 6243-14-16, the feed contained only propylene oxide, methanol and acetone. The purpose behind the use of a synthetic feed was to demonstrate the reduction in propylene oxide loss for a given set of operating conditions.

By way of comparison, about a 70-fold reduction in propylene oxide loss may be realized with a propylene oxide feed containing impurities in addition to methanol by lowering the column pressure from 36 to 18 psia and the use of an acetone/water extractive agent over that of pure water.

Table II is a presentation of the percent propylene oxide loss with respect to the location where the acetone enters the tower. The percent acetone is expressed as the amount of acetone entering the column at the feed and solvent locations to the total amount of feed and solvent over the material balance period in question. It is clear from the data that propylene oxide loss is decreased as the percentage of acetone in the system is increased for a given set of operating parameters.

For comparison purposes, Trials 6243-14-08 and 6243-1416 were conducted to test if there was any advantage to adding the acetone to the solvent over simply adding it to the feed. The starting feed material consisted only of methanol and propylene oxide. It is apparent that only a slight advantage, if any at all, is gained when acetone is added to the solvent instead of the feed.

TABLE I

METHANOL REMOVAL FROM PROPYLENE OXIDE BY EXTRACTIVE DISTILLATION
Reference NB: 6204-

| Pg/Ln | Pressure (psia) | Bottoms Temp (C.) | Solvent | Feed/Solvent | Reflux Ratio | % MeOH Reduction | % PO Loss |
|---|---|---|---|---|---|---|---|
| 09-20 | 36 | 101 | $H_2O$ | 13/1 | 8/1 | >95 | 7.0 |
| 25-14 | 36 | 90 | Acetone/$H_2O$ (27/73) | 7/1 | 8/1 | >95 | 2.2 |
| 25-24 | 36 | 97 | Acetone/$H_2O$ (27/73) | 6/1 | 8/1 | >95 | 2.1 |
| 24-30 | 36 | 86 | Acetone/$H_2O$ (27/73) | 8/1 | 8/1 | >95 | 1.7 |
| 08-05 | 18 | 88 | $H_2O$ | 14/1 | 8/1 | >95 | 0.8 |
| 28-20 | 18 | 76 | Acetone/$H_2O$ (23/77) | 17/1 | 5/1 | >95 | 0.1 |
| *6204-18-28 | 36 | 111 | $H_2O$ | 7/1 | 8/1 | 93 | 3.2 |
| *6243-14-16 | 18 | 78 | $H_2O$ | 15/1 | 8/1 | 92 | 0.4 |
| *6243-14-08 | 18 | 78 | Acetone/$H_2O$ (18/82) | 17/1 | 8/1 | 89 | 0.3 |

*Synthetic Blend

Notes:
1. The column used to generate the above data consisted of approximately 28 theoretical trays with the propylene oxide feed being introduced 7 trays above the reboiler and the solvent 14 trays above the reboiler.
2. Table I shows that for a given pressure, propylene oxide loss decreases when a water/acetone solvent is used over that of pure water. The bottoms temperature (reboiler) is also reduced when the blend solvent is used at a given pressure. This is important in reducing converion of propylene oxide to propylene glycol. It is also known that propylene oxide loss is reduced when the operating pressure is reduced.

TABLE II

PERCENT ACETONE ADDED AT FEED AND SOLVENT POINTS IN TOWER

| Pg/Ln | % PO Loss | % Acetone Solvent | % Acetone Feed | % Acetone Total |
|---|---|---|---|---|
| Reference: 6204- | | | | |
| 09-20 | 7.0 | 0.0 | 0.9 | 0.9 |
| 25-14 | 2.2 | 3.2 | 0.1 | 3.3 |
| 25-24 | 2.1 | 3.6 | 0.1 | 3.7 |
| 24-30 | 1.7 | 3.0 | 0.1 | 3.1 |
| 08-05 | 0.8 | 0.0 | 0.9 | 0.9 |
| 28-20 | 0.1 | 1.3 | 0.1 | 1.4 |
| Reference: 6243- | | | | |
| *14-08 | 0.3 | 1.0 | 0.0 | 1.0 |
| *14-16 | 0.4 | 1.0 | 0.0 | 1.0 |

*Synthetic Blend

1. The percent acetone is expressed as the amount of acetone entering the column at the feed and solvent locations, respectively, to the total amount of feed and solvent over the material balance period in question.
2. Table II shows that for "real" crude propylene oxide that propylene oxide loss is decreased as the amount of acetone in the system is increased whether added by feed or solvent.
3. The percent propylene oxide lost is that which is converted to propylene glycol plus that leaving the bottom of the tower as propylene oxide.
4. Trials 18-28 and 14-8 were performed with synthetic feed, i.e., only propylene oxide and methanol. In Trial 14-16, the acetone was added to the feed rather than the solvent. The balance of the data was obtained with impure propylene oxide material being comprised of:

| Component | Weight % |
|---|---|
| Propylene Oxide | 91 to 99 |
| Methanol | 0.01 to 0.05 |
| Acetone | 0.10 to 1.0 |
| Others | 0.4 to 3.3 |
| Water | 0.08 to 4.0 |

Having thus described our invention, what is claimed is:

1. An extractive distillation process for the distillation of impure propylene oxide in a distillation column containing a reflux condenser and a reboiler to remove contaminants, including methanol, from the impure propylene oxide with a substantially reduced loss of propylene oxide during the distillation which comprises the steps of:

distilling said impure propylene oxide in an distillation column containing at least 25 theoretical plates while introducing said impure propylene oxide feedstock into the lower half of said distillation column, said impure propylene oxide feedstock comprising propylene oxide contaminated with from about 50 to about 1000 ppm of methanol and from about 0 to about 1 wt. % of acetone, introducing an extractive distillation agent consisting essentially of an acetone/water blend containing about 20 to about 30 wt. % of acetone and, correspondingly, about 80 to 70 wt. % of water at a point 4 to 7 theoretical plates above the said impure propylene oxide feed point, said extractive distillation agent being introduced into said distillation column in the ratio of said feedstock to said extractive distillation agent of from about 5:1 to about 20:1, withdrawing an overhead distillate fraction from said distillation column consisting essentially of propylene oxide contaminated with not more than about 60 ppm of propylene oxide, not more than about 0.02 wt. % of acetone and not more than about 0.3 wt. % of water, and withdrawing an aqueous bottoms distillation fraction from said distillation column containing substantially all of the methanol, acetone and water introduced into said distillation column.

2. A method as in claim 1 wherein said distillation column is operated at a pressure of about 0 to about 30 psig and a reboiler temperature within the range of about 60° to about 100° C.

3. A method as in claim 2 wherein said distillation column is operated at a reflux ratio of from about 5:1 to about 10:1.

4. A method as in claim 3 wherein said overhead propylene oxide fraction contains not less than 95 wt. % of the propylene oxide charged to said distillation column and wherein said bottoms distillation fraction contains not more than about 1 wt. % of the propylene oxide charged to said distillation column.

5. An extractive distillation process for the distillation of impure propylene oxide in a distillation column containing a reflux condenser and a reboiler to remove contaminants, including methanol, from the impure propylene oxide with a substantially reduced loss of propylene oxide during the distillation which comprises the steps of:

introducing an impure proplene oxide feedstock into the lower half of a distillation column containing at least 25 theoretical plates, said impure propylene oxide feedstock comprising propylene oxide contaminated with from about 50 to about 1000 ppm of methanol and from about 0 to about 1 wt. % of acetone, introducing an extractive distillation agent consisting essentially of an acetone/water blend containing about 20 to about 30 wt. % of acetone and, correspondingly, about 80 to about 70 wt. % of water at a point about 4 to 7 theoretical plates above the said impure propylene oxide feed point, said extractive distillation agent being introduced into said distillation column in the ratio of said feedstock to said extractive distillation agent of from about 5:1 to about 20:1, fractionating said impure propylene oxide feedstock in said distillation column under distillation conditions including a pressure of about 0 to about 30 psig, a reflux ratio of from about 5:1 to about 10:1, a reboiler temperature within the range of about 60° to about 100° C. and a top temperature of about 35° to about 70° C., withdrawing an overhead purified propylene oxide distillate fraction from said distillation column consisting essentially at least about 95 wt. % of the propylene oxide charged to said distillation column, said purified propylene oxide distillate fraction being contaminated with not more than about 60 ppm of methanol, not more than about 0.02 wt. % of acetone and not more than about 0.3% of water, and withdrawing an aqueous bottoms distillation fraction from said distillation column containing not more than about 1 wt. % of the propylene oxide charged to said distillation column and substantially all of the methanol, acetone and water introduced into said distillation column.

6. In a method for the separation of impurities from an impure propylene oxide fraction obtained by the reaction of tertiary butyl hydroperoxide with propylene in solution in tertiary butyl alcohol in the presence of a soluble epoxidation catalyst, said impure propylene oxide fraction being contaminated with impurities including methyl formate, acetaldehyde, acetone, methanol and water, the improved method of purifying said impure propylene oxide fraction in a distillation zone containing four distillation columns, each of which is equipped with a reflux condenser and a reboiler, which comprises the steps of:

a. charging said impure propylene oxide fraction to the first of said distillation columns, said first distillation column being operated under distillation conditions including a pressure of about 10 to about 70 psig, a reboiler temperature of about 50° to about 90° C. and a top reflux temperature of about 40° to about 80° C. selected for the separation of an overhead distillate fraction containing acetaldehyde and substantially all of the methyl formate in said impure propylene oxide fraction and to provide a heavier distillation fraction comprising substantially all of the propylene oxide, methanol, acetone and water originally present in said impure propylene oxide fraction, b. introducing said heavier distillation fraction into the lower half of the second of said distillation columns, said second distillation column containing at least 25 theoretical plates, said heavier distillation fraction comprising propylene oxide contaminated with from about 50 to about 1000 ppm of methanol and from about 0 to about 1 wt. % of acetone, c. introducing an extractive distillation agent into said second distillation column, said extractive distillation agent consisting essentially of an acetone/water blend containing about 20 to about 30 wt. % of acetone and, correspondingly, about 80- to 70 wt. % of water, said extractive distillation agent being introduced into said second distillation column at a point about 4 to 7 theoretical plates above the crude propylene oxide feed point, said extractive distillation agent being introduced into said distillation column in the ratio of said feedstock to said extractive distillation agent of from about 5:1 to about 20:1, d. fractionating said heavier distillation fraction in said second distillation column under distillation conditions including a pressure of about 0 to about 30 psig, a reflux ratio to impure propylene oxide feed of from about 5:1 to about 10:1, and a reboiler temperature within the range of about 60° to about 100° C., e. withdrawing an overhead further purified propylene oxide distillate fraction from said second distillation column consisting essentially of at least about 95 wt. % of the propylene oxide charged to said second distillation column, said further purified propylene oxide distillate fraction being contaminated with not more than about 60 ppm of methanol, not more than about 0.02 wt. % of acetone and not more than about 0.3 wt. % of water, f. withdrawing an aqueous bottoms distillation fraction from said second distillation column containing not more than about 1 wt. % of the propylene oxide charged to said first distillation column and substantially all of the methanol, acetone and water introduced into said distillation column, g. introducing said further purified propylene oxide distillate fraction into the third of said distillation columns and operating said third distillation column at about atmospheric pressure under distillation conditions including a reflux temperature of about 40° to about 45° C. and a reboiler temperature of about 45° to about 50° C. selected to provide a purified substantially anhydrous propylene oxide distillate fraction and an aqueous heavier distillation fraction containing substantially all of the water and acetone charged to said third distillation column, h. recycling said aqueous heavier distillation fraction from said third distillation column to said second distillation column as reflux, and i. introducing said aqueous bottoms distillation fraction from said second distillation column into the fourth of said distillation columns and operating said fourth distillation column at about atmospheric pressure under distillation conditions including a reflux temperature of about 60° to about 65° C. and a reboiler temperature of about 115° to about 125° C. selected to provide an acetone distillate fraction and a waste water heavier distillation fraction containing substantially all of the water and other impurities charged to said second distillation column.

* * * * *